United States Patent
Pagan

Patent Number: 5,771,889
Date of Patent: Jun. 30, 1998

[54] LARYNGEAL MASK AIRWAYS

[75] Inventor: Eric Pagan, Folkestone, England

[73] Assignee: Smiths Industries PLC, London, England

[21] Appl. No.: 606,307

[22] Filed: Feb. 23, 1996

[30] Foreign Application Priority Data

Mar. 14, 1995 [GB] United Kingdom .................. 9505134

[51] Int. Cl.$^6$ .................................................. A61M 29/00
[52] U.S. Cl. ................................ 128/207.15; 128/200.23; 604/96
[58] Field of Search ......................... 128/207.14, 207.15, 128/206.26, 200.24, 200.26; 604/96, 97, 98, 99, 100, 101, 102, 103, 174

[56] References Cited

U.S. PATENT DOCUMENTS 5,297,547  3/1994  Brain .
5,477,851  12/1995  Callaghan et al. .

FOREIGN PATENT DOCUMENTS 0 389 272  9/1990  European Pat. Off. .

Primary Examiner—Vincent Millin
Assistant Examiner—Robert N. Wieland
Attorney, Agent, or Firm—Pollock, Vande Sande & Priddy

[57] ABSTRACT

A laryngeal mask assembly has a mask subassembly at its patient end with an inflatable ring and a diaphragm extending within the ring. The mask subassembly is attached to a tube by means of a mount comprising a backing plate and a tubular extension fitted on the patient end of the tube. The diaphragm is attached to the backing plate and the plate overlaps the patient end of the sealing ring extending close to the patient end of the assembly so as to inhibit rearward deflection of the patient end of the sealing ring.

4 Claims, 2 Drawing Sheets

PRIOR ART

LARYNGEAL MASK AIRWAYS

BACKGROUND OF THE INVENTION

This invention relates to laryngeal mask airways.

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat No. 5355879, U.S. Pat No. 5305743, U.S. Pat No. 5297547, U.S. Pat No. 5282464, GB 2267034, U.S. Pat No. 5249571, U.S. Pat No. 5241956, U.S. Pat No. 5303697, GB 2249959, GB 2111394, EP 448878, U.S. Pat No. 4995388, GB 2205499 and GB 2128561.

Laryngeal masks have several advantages over endotracheal tubes, which are longer and seal with the trachea below the vocal folds. One problem, however, with laryngeal masks is that insertion can cause trauma to the pharyngeal wall. This is because the tip of the mask has a tendency to stick in the pharynx as a result of the sharp turn it has to negotiate before it seats itself in the hypopharynx. These problems have been reported in, for example, Anaesthesia 1989; 44: 703 by van Heerden and Kirrage. Although the risk of damage can be reduced by ensuring that the head of the patient is correctly positioned during insertion, where the anaesthetist is not completely familiar with the correct technique, there is still an associated risk of trauma. Blood is often seen on the laryngeal mask when it is removed, even when the anaesthetist is experienced in the technique. The problem can be aggravated because, in conventional airways, when the mask is deflated for insertion, this causes the forward tip of the airway (as provided by the deflated leading edge of the mask) to curve in the opposite direction from the main tubular part of the airway. Because of this, the tip tends to curve rearwardly towards the hard palate, increasing the risk of trauma and morbidity. There can also be a risk, when the tip rubs during insertion, that the mask can evert and enter the nasal passage.

In GB 2259454 there is described an introducer for a laryngeal mask, which can be used to facilitate insertion and reduce the risk of injury to the patient. It is desirable, however, in some instances to avoid the need to use a separate introducer.

BRIEF SUMMARY OF THE INVENTION

It is an object of the present invention to provide an improved laryngeal mask assembly.

According to the present invention there is provided a laryngeal mask assembly including a mask subassembly and an elongate tube that opens at its patient end into the mask subassembly, the mask subassembly being adapted during use to locate in the hypopharynx and to open on its forward side to the patient's airway, the mask subassembly having an inflatable sealing ring and a generally planar backing member extending on the rear side of the mask subassembly to overlap the patient end of the sealing ring such that, when the sealing ring is deflated for insertion, the backing member inhibits rearward deflection of the patient end of the sealing ring.

The mask subassembly preferably includes a mount member, the backing member being a part of the mount member and the mount member including a tubular extension attached with the elongate tube. The mask subassembly may include a mask portion, the sealing ring being a part of the mask portion, the mask portion including a diaphragm extending within the sealing ring and attached to the backing member, the diaphragm having an aperture therethrough opening into the tube. The backing member preferably extends close to the patient end of the assembly.

A laryngeal mask assembly according to the present invention, will now be described, by way of example, with reference to the accompanying drawings.

DETAILED DESCRIPTION OF THE PREFERRED EMBODIMENT

Figure 1:
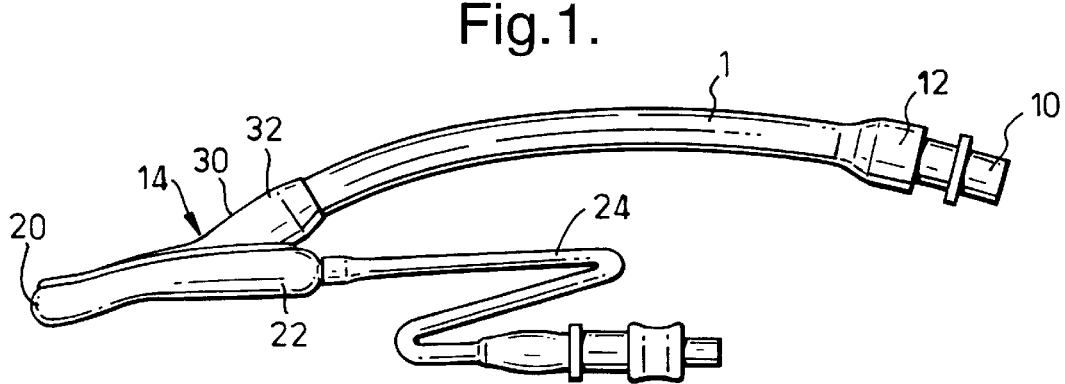
FIG. 1 is a side elevation view of the assembly.

The assembly comprises a bendable tube 1 of a plastics material, such as PVC, with a coupling 10 at its machine end 12. The tube 1 is curved along its length and is joined at its patient end to a mask subassembly 14 comprising a mask portion 20 and a mount 30.

Figure 4:
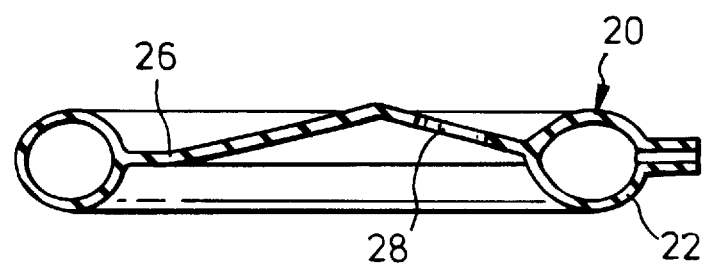
FIG. 4 is a sectional side elevation view of the mask subassembly before assembly.

The mask portion 20 is similar to that described in GB 2111394, being formed of a soft, flexible plastics or rubber material. The mask portion 20 has a peripheral annular sealing ring 22 connected with an inflation line 24 by which the ring can be inflated and deflated with air. The sealing ring 22 is of elliptical shape with its major axis extending in the same plane as the tube 1. Within the ring 22, the mask portion has a flexible diaphragm 26 with a shallow conical shape. An opening 28 in the diaphragm 26 communicates with the bore through the tube 1. In its natural state, before the mask portion 20 is attached to the mount 30, the diaphragm 26 is attached with the sealing ring 22 at a midpoint around its thickness, in the conventional manner, as shown in FIG. 4.

Figure 2:
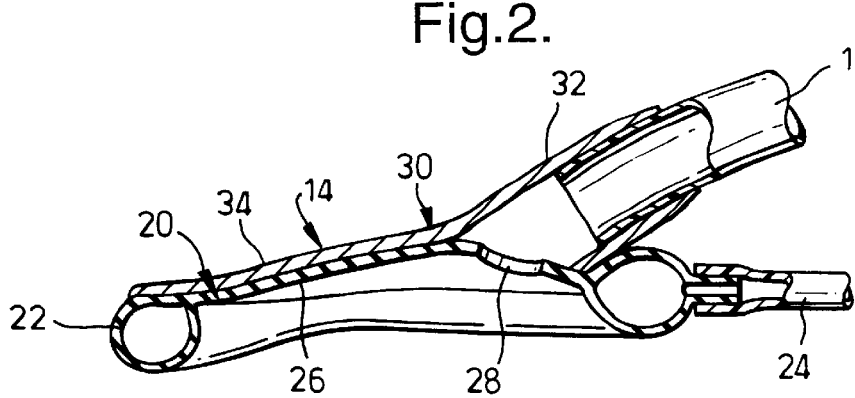
FIG. 2 is an enlarged sectional side elevation view of the mask subassembly.
Figure 3:
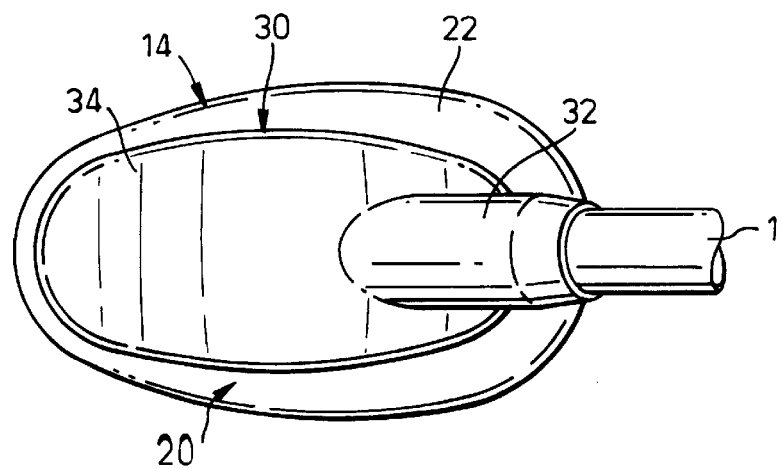
FIG. 3 is a view from above of the rear of the mask subassembly.

The mask portion 20 is attached with the patient end of the tube I by means of the mount 30 made of the same material as the mask portion itself. The mount 30 comprises a short tubular extension 32 extending a short distance along the outside of the machine end of the tube I and sealed with it by means of welding, solvent or an adhesive. The patient end of the tubular extension 32 is aligned with the opening 28 in the diaphragm 26. The mount 30 is completed by a backing plate 34 formed integrally with the tubular extension 32. The backing plate 34 is of generally elliptical shape and extends forwardly from the patient end of the tubular extension. The lower, forward side of the backing plate 34 is secured to the upper, rear surface of the diaphragm 26 and overlaps the sealing ring 22 so that the diaphragm is pulled up and the patient end of the sealing ring is twisted anticlockwise (as viewed in FIG. 2). This causes the lower surface of the patient end of the mask portion 20 to bend down or forwardly. When assembled, the peripheral edge of the diaphragm 26 at the patient end side of the sealing ring 22 is contiguous with the upper, rear face of the ring so that the ring and diaphragm form a smooth continuation where they meet over the tip region. The backing plate 34 extends to within a few millimetres of the patient end of the assembly and is smoothly rounded so as to reduce the risk of trauma.

Figure 5:
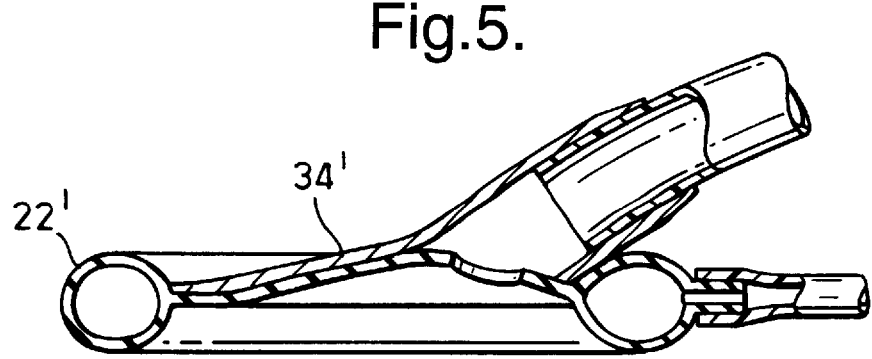
FIG. 5 is a sectional side elevation view of a mask subassembly of a conventional, prior art assembly.

In previous laryngeal mask assemblies, as shown in FIG. 5, the backing plate 34' does not overlap the sealing ring 22', so the sealing ring projects above the backing plate at its patient end. When air is pulled out of the sealing ring of these conventional assemblies, the sealing ring collapses and tends to bend upwardly or rearwardly at its patient end. Because the sealing ring 22' is substantially rigid when collapsed, this rearwardly-projecting tip can increase the risk of trauma to the hard palate during insertion.

In the present assembly, the patient end of the sealing ring 22 cannot project rearwardly when deflated, because the backing plate 34 extends over the sealing ring in this region. In this way, the rear surface of the mask subassembly 14 remains substantially flat during insertion. This reduces the risk of trauma, makes insertion easier and reduces the risk of the patient end being incorrectly inserted in the nasal passage. Because of this, the need to use an introducer is reduced.

What I claim is:

1. A laryngeal mask assembly comprising: a mask subassembly, said mask subassembly being adapted during use to locate in the hypopharynx and to open on its forward side to the patient's airway; and an elongate tube, said tube opening at its patient end into said mask subassembly, wherein said mask subassembly has an inflatable sealing ring and a generally planar backing member extending on a rear side of said mask subassembly to overlap a patient end of said sealing ring such that, when said sealing ring is deflated for insertion, said backing member inhibits rearward deflection of the patient end of said sealing ring.

2. A laryngeal mask assembly according to claim 1, wherein said mask subassembly includes a mount member, wherein said backing member is a part of said mount member, and wherein said mount member includes a tubular extension attached with said elongate tube.

3. A laryngeal mask assembly according to claim 1, wherein said mask subassembly includes a mask portion, wherein said sealing ring is a part of said mask portion, wherein said mask portion includes a diaphragm extending within said sealing ring and attached to said backing member, and wherein said diaphragm has an aperture therethrough opening into said tube.

4. A laryngeal mask assembly according to claim 1, wherein said backing member extends close to a patient end of said assembly.

\* \* \* \* \*